United States Patent
Duflot et al.

(10) Patent No.: US 10,479,812 B2
(45) Date of Patent: Nov. 19, 2019

(54) FIBER-RICH MALTOOLIGOSACCHARIDES HAVING LOW GLUCOSE BIOAVAILABILITY, METHOD OF MANUFACTURE THEREOF AND USE THEREOF IN HUMAN FOOD AND ANIMAL FEED

(71) Applicant: Roquette Freres, Lestrem (FR)

(72) Inventors: Pierrick Duflot, La Couture (FR); Jean-Michel Roturier, Armentieres (FR); Baptiste Boit, La Gorgue (FR); Pierre Lanos, La Bassee (FR); Heike Jerosch, Estaires (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 15/551,251

(22) PCT Filed: Feb. 16, 2016

(86) PCT No.: PCT/FR2016/050355
§ 371 (c)(1),
(2) Date: Aug. 15, 2017

(87) PCT Pub. No.: WO2016/132064
PCT Pub. Date: Aug. 25, 2016

(65) Prior Publication Data
US 2018/0037599 A1    Feb. 8, 2018

(30) Foreign Application Priority Data

Feb. 16, 2015 (FR) ...................................... 15 51274

(51) Int. Cl.
| C07H 1/00 | (2006.01) |
| C07H 3/00 | (2006.01) |
| A23L 33/21 | (2016.01) |
| A23K 20/163 | (2016.01) |
| C07H 3/06 | (2006.01) |

(52) U.S. Cl.
CPC .............. *C07H 1/00* (2013.01); *A23K 20/163* (2016.05); *A23L 33/21* (2016.08); *C07H 3/00* (2013.01); *C07H 3/06* (2013.01); *A23V 2002/00* (2013.01)

(58) Field of Classification Search
None
See application file for complete search history.

(56) References Cited

U.S. PATENT DOCUMENTS

| 4,843,154 A * | 6/1989 | Klein ..................... C07H 15/04 |
| | | 516/43 |
| 5,264,568 A | 11/1993 | Yamada et al. |
| 2007/0172931 A1 | 7/2007 | Harrison et al. |
| 2009/0297690 A1* | 12/2009 | Nehmer ................ A23L 29/212 |
| | | 426/661 |

FOREIGN PATENT DOCUMENTS

| EP | 0 368 451 A2 | 5/1990 |
| EP | 0 530 111 A1 | 3/1993 |
| EP | 0 675 137 A2 | 10/1995 |
| EP | 1 006 128 A1 | 6/2000 |
| GB | 1422294 † | 1/1976 |
| WO | WO 2008/085529 A2 | 7/2008 |
| WO | WO 2013/128121 A1 | 9/2013 |
| WO | WO 2014/145276 A1 | 9/2014 |
| WO | WO 2014/158777 A1 | 10/2014 |

OTHER PUBLICATIONS

S. Hakomori et al., "A Rapid Permethylation of Glycolipid, and Polysaccharide Catalyzed by Methylsulfinyl Carbanion in Dimethyl Sulfoxide." The Journal of Biochemistry, vol. 55, No. 2, pp. 205-208, 1964.
Ferenci, et al.; Substrate specificity of the *Escheria coli* maltodextrin transport system and its component proteins; pp. 44-50; Biochimica et Biophysica Acta 860 (1986)†

\* cited by examiner
† cited by third party

*Primary Examiner* — Layla D Berry

(57) ABSTRACT

The present invention relates to maltooligosaccharides, the content of α-1,4-glycosidic bonds of which is between 70% and 80% of the total number of 1,4-type glycosidic bonds. The invention also relates to the method for manufacturing these maltooligosaccharides. Said maltooligosaccharides afford all the benefits of fiber-based foods, with an extremely low nutritional value. Such a compromise is particularly advantageous for use in healthy balanced diets, but also in the treatment and/or prevention of the pathology of diabetes. The invention also relates to the use of said maltooligosaccharides in the fields of human food and animal feed.

21 Claims, 2 Drawing Sheets

FIBER-RICH MALTOOLIGOSACCHARIDES HAVING LOW GLUCOSE BIOAVAILABILITY, METHOD OF MANUFACTURE THEREOF AND USE THEREOF IN HUMAN FOOD AND ANIMAL FEED

CROSS REFERENCE TO RELATED APPLICATIONS

This application is the U.S. national stage application of International (PCT) Patent Application Serial No. PCT/FR2016/050355, filed Feb. 16, 2016, which claims the benefit of FR Application No. 1551274, filed Feb. 16, 2015. The disclosures of these two applications are hereby incorporated by reference herein in their entirety.

FIELD OF THE INVENTION

The present invention relates, according to a first embodiment, to maltooligosaccharides, the content of α-1,4-glycosidic bonds, of which is between 70% and 80% of the total number of 1,4-type glycosidic bonds. According to a second embodiment, the maltooligosaccharides especially have a content of α-1,4 bonds of between 65% and 83% of the total number of 1,4 bonds and/or a ratio of the total number of 1,4-bonds to the total number of 1,6 bonds of greater than 1 and/or a content of α-1,6-bonds of between 35% and 58% of the total number of 1,6-glycosidic bonds. The term "maltooligosaccharides" refers here to saccharides comprising at least 2 saccharide units, that is to say for example to saccharides having a degree of polymerization $D_P$ of between 2 and 30, said saccharides comprising at least one carbohydrate which is maltose. The term "polysaccharides", also used in the present application, refers in a broader sense to saccharides comprising at least 2 saccharide units, that is to say for example to saccharides having a degree of polymerization $D_P$ of between 2 and 30.

Particularly advantageously, fine-tuning the content of α-1,4-glycosidic bonds leads to unique products in accordance with the present invention, demonstrating an ideal compromise between relatively high fiber-richness and very low glucose bioavailibility with regard to the organism. Thus, as yet unidentified mixed products are available which afford all the benefits of fiber-based foods, with an extremely low nutritional value. Such a compromise is particularly advantageous for use in healthy balanced diets, but also in the treatment and/or prevention of the pathology of diabetes.

The invention also relates to an original method which is very simple to implement for manufacturing these maltooligosaccharides, in which a mixture of a maltose-rich aqueous carbohydrate solution, at least one polyol and at least one acid undergoes a heat treatment at high temperature (between 130° C. and 300° C.) under reduced pressure. The choice of starting raw materials, and especially of the maltose-rich aqueous carbohydrate solution, but also the duration of the treatment, are some of the means by which the content of α-1,4-bonds can be regulated to within the range mentioned above.

A final subject of the present invention consists of the use of the maltooligosaccharides according to the invention in human food and animal feed.

TECHNICAL PROBLEM AND PRIOR ART

For several years, there has been some interest among the general public for new, fiber-based diets. The term "dietary fiber" is intended to mean plant parts which are not hydrolyzed by enzymes during digestion. They are residual substances which come from the cell wall or cytoplasm of plants, consisting of complex mixtures of carbohydrates which have been identified as non-starch polysaccharides.

Among dietary fiber, a distinction is made between insoluble fibers and water-soluble fibers. Oats, barley, fruits, fresh vegetables and pulses (beans, lentils, chickpeas) constitute good sources of soluble fibers, whereas whole grain cereals and whole grain bread are rich in insoluble fibers. Insoluble fibers, such as cellulose, resistant starches, corn fibers (spent grain) or soya fibers, have an essentially mechanical role in the gastrointestinal tract. They are only very slightly fermented by colonic flora, and contribute to reducing intestinal transit time by a ballast effect. Insoluble fibers thus contribute to preventing constipation by increasing the weight of the stools and by reducing the duration of intestinal transit.

Soluble fibers, such as pectin and inulin, which cannot be digested by the intestinal enzymes in humans or animals, are fermented by the colonic flora. This fermentation releases short-chain fatty acids in the colon, the effect of which is to reduce the pH thereof and, consequently, to limit the development of pathogenic bacteria and to stimulate the development of beneficial bacteria.

Alongside these compounds which are predominantly extracted from plants, there are molecules derived from starch or from the products of the partial or total hydrolysis thereof. Polydextrose, for example, is synthesized by random polymerization of glucose in the presence of sorbitol and a suitable acid catalyst (such as citric acid) at high temperature. Said polydextrose is widely used in food as a filling agent and as a low-calorie ingredient.

More generally, glucose polymers are conventionally manufactured industrially by hydrolysis of natural or hybrid starches and derivatives thereof. These starch hydrolyzates (dextrins, pyrodextrins, etc.) are thus produced by acid or enzymatic hydrolysis of cereal starch or tuber starch. They actually consist of a mixture of glucose and glucose polymers of highly varied molecular weights. Said hydrolyzates have a broad distribution of saccharides containing both linear structures (α-1,4-glycosidic bonds) and branched structures (α-1,6-glycosidic bonds).

By way of examples, patent applications EP 0 368 451 and U.S. Pat. No. 5,264,568 describe a method for preparing pyrodextrins, the dietary fiber characteristics of which are strengthened by the action of an α-amylase or several successive α-amylases on a dextrin or pyrodextrin, in solution at high temperature.

In patent application EP 0 530 111, indigestible dextrins obtained by extrusion of an acidified dehydrated corn starch under specific conditions are described. This treatment may be supplemented by the action of a heat-resistant α-amylase.

The applicant company itself also described, in its patent application EP 1 006 128, branched maltodextrins having between 22% and 35% 1,6-glycosidic bonds (both α and β type), a content of reducing sugars of less than 20%, a polydispersity index of less than 5 and a number-average molecular weight $M_n$ at most equal to 4500 g/mol. These branched maltodextrins are most of all indigestible in character and consequently this reduces their calorific value by preventing their assimilation in the small intestine; they are therefore essentially a source of indigestible fibers.

The applicant company also described and protected, in its patent application WO 2013/128121, hyperbranched maltodextrins of low molecular weight, i.e. having a dextrose equivalent (DE) of between 8 and 15 and a molecular weight $M_w$ of between 1700 and 3000 Daltons, characterized by a content of 1,6-glycosidic bonds (both α and β type) of between 30% and 45%, a content of soluble indigestible fibers of between 75% and 100% (according to AOAC method no. 2001-03) and noteworthy hypoglycemic properties which are reflected both in vitro and in situ by a limiting effect with respect to the standard maltodextrin digestion.

Patent application WO 2014/158777 is also known, which describes a carbohydrate which can be used as food ingredient (especially as a calorie-reducing agent) containing both linear and branched oligomers, the sugar content of which is between 5% and 25% by weight of the dry weight thereof, with a fiber content of between 10% and 70% of the dry weight thereof. Another of its features is having a content of polysaccharides with high molecular weights, such that the vicosity thereof is less than 16 000 cPs at 100° F. and a solids content of 75%.

Patent applications U.S. Pat. No. 7,608,436 and WO 2008/085529 are also known, which describe a poorly digestible food product based on oligosaccharides. Said oligosaccharides have here a content of branched oligomers which is greater than the content of linear oligomers, and a concentration of non-linear oligomers with a degree of polymerization of greater than or equal to 3 which is greater than 20% by dry weight.

Finally, patent application WO 2014/145276 is known, which describes compositions based on carbohydrates having a low calorific value. Various families of carbohydrates are described and claimed therein, especially through their content of molecules with a degree of polymerization of 1 and 2, of 1,6-bonds, of total 1,4- and 1,6-bonds, through the ratio of the content of 1,4- to 1,6-bonds and finally through their molecular weight.

Moreover, the products sold under the names Promitor (Tate & Lyle), Fibersol (Matsutani), Litesse (Dupont Danisco) and Nutriose (Roquette) are known, which are all more or less fiber-rich products based on polysaccharides.

It arises from the above text that there have been continual innovations at least over the last 10 years in the field of fiber-rich products liable to have advantages for humans in the context of new, healthier and more balanced diets. It may especially be most interesting to have a product which is both fiber-rich and liable to release only a very small amount of glucose when it is digested by the organism, or alternatively to have very long glucose release kinetics with regard to the organism. With this in mind, the latter property appears potentially to be highly advantageous in the context of diets for diabetic patients and/or with a view to limiting the risks of exposure regarding this pathological condition.

SUMMARY OF THE INVENTION

To this end, the applicant company has pursued much laborious study and research which has enabled it to develop products which meet these requirements. According to one embodiment, the products in question may be defined as maltooligosaccharides, especially having a content of α-1, 4-bonds of between 70% and 80% of the total number of 1,4-glycosidic bonds. According to a second embodiment, the products in question may be defined as maltooligosaccharides, especially having a content of α-1,4-bonds of between 65% and 83% of the total number of 1,4-bonds and/or a ratio of the total number of 1,4-bonds to the total number of 1,6-bonds of greater than 1 and/or a content of α-1,6-bonds of between 35% and 58% of the total number of 1,6-glycosidic bonds.

Compared to the products of the prior art known to the applicant, some maltooligosaccharides of the present application have quite specific contents of α-1,4-bonds which have hitherto never been described or achieved. At the same time, and according to the knowledge of the applicant, there are, in the prior art, no products of the maltooligosaccharide type having a content of α-1,4-bonds of between 70% and 80% of the total number of 1,4-bonds or maltooligosaccharides especially having a content of α-1,4-bonds of between 65% and 83% of the total number of 1,4-bonds and/or a ratio of the total number of 1,4-bonds to the total number of 1,6-bonds of greater than 1 and/or a content of α-1,6-bonds of between 35% and 58% of the total number of 1,6-glycosidic bonds.

Moreover, by virtue of an original approach combining proton nuclear magnetic resonance ($^1$H NMR) and gas chromatography, the applicant has been able to clarify the influence of the parameter retained (i.e. the content of α-1,4-bonds relative to the sum total of 1,4-bonds) on the fiber content of the final product and the bioavailibility of glucose with regard to the organism.

Indeed, NMR gives access to the proportions of total α-1,4- and α-1,6-glycosidic bonds on the one hand, and to other glycosidic bonds on the other. Mass spectrometry, for its part, makes it possible to access the proportions of total 1,4-, 1,6-, 1,2- and 1,3-glycosidic bonds, but without any indication as to the nature of the anomer. The latter technique is employed within the context of the "Hakomori" method which is well known to those skilled in the art and which precisely makes it possible to quantify the contents of total 1,4-, 1,6-, 1,2- and 1,3-glycosidic bonds. This method, described for the first time over 50 years ago (Hakomori, S., 1964, J. Biol. Chem., 55, 205) is nowadays widely used within the scientific community (see especially patent application EP 1 006 128, already cited in the present application).

On the basis of these studies and an approach of this kind, the applicant has demonstrated the critical role of the content of α-1,4-bonds relative to the sum total of 1,4-type glycosidic bonds in obtaining:
  a sufficient fiber supply to maintain the abovementioned beneficial effects linked to a fiber-rich diet,
  extremely low glucose bioavailability, especially well below that shown by the majority of products currently commercially available.

This glucose bioavailibility refers to the amount of glucose released after digestion by intestinal enzymes.

Quite advantageously, the very precise regulation of the content of α-1,4-bonds relative to the sum total of 1,4-type glycosidic bonds to within the abovementioned range is the main means by which it is possible to arrive at the ideal compromise between this sufficient fiber supply and this extremely low glucose bioavailability.

Moreover, by means of a very simple method, the applicant has been able to synthesize the maltooligosaccharides which are the subject of the present invention. Put very simply, this method consists initially in providing a maltose-rich aqueous carbohydrate solution, in adding at least one polyol and at least one acid, and then in carrying out a heat treatment at high temperature (between 130° C. and 300° C.) under reduced pressure.

Finally, it should be noted that throughout the present application, the fiber content, the amount of glucose released or accessible after enzymatic digestion, and the contents of glycosidic bonds are determined according to strict protocols which are the subject of a very detailed description in the experimental section relating to said application.

DETAILED DESCRIPTION OF THE INVENTION

Figure 1:
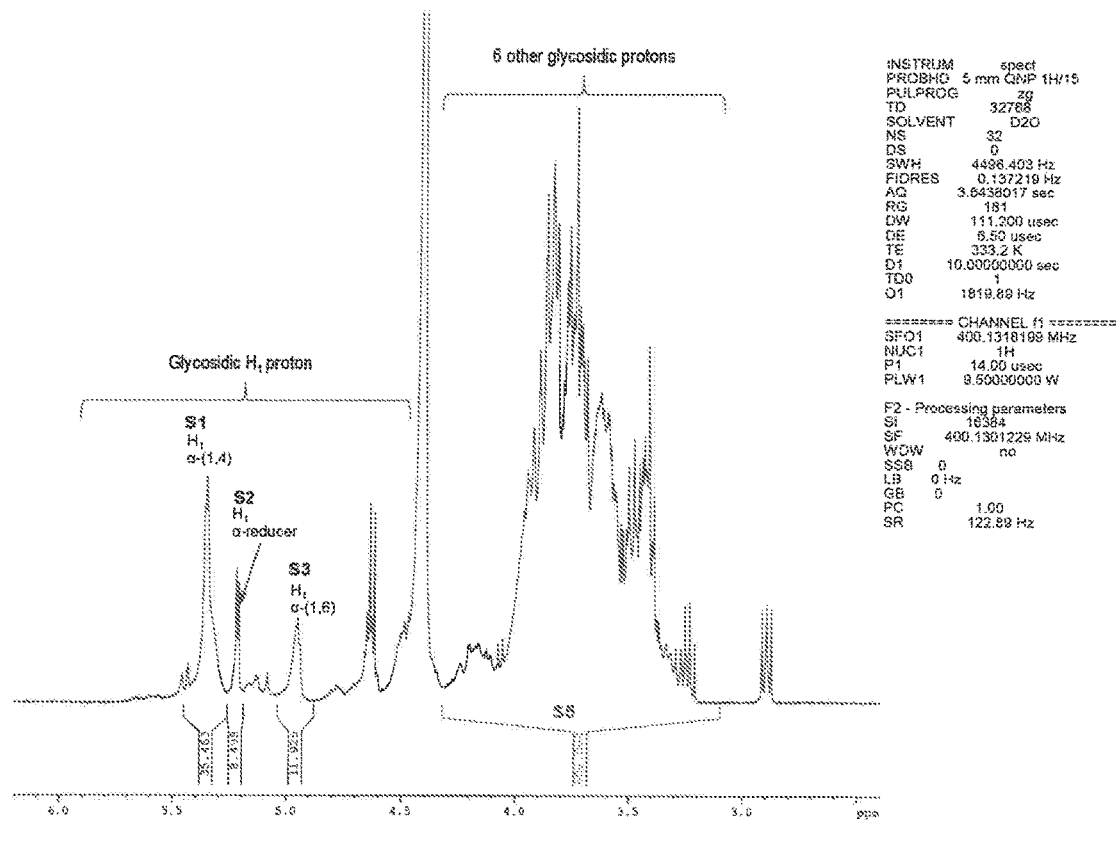
FIG. 1 shows signal integration and limits of integration.

A first subject of the invention is based on a method for manufacturing maltooligosaccharides comprising the steps consisting in:
a) providing an aqueous solution of at least two carbohydrates, characterized in that 40% to 95% of the dry weight of said solution consists of maltose,
b) placing the aqueous solution resulting from step a) in contact with at least one polyol and at least one inorganic or organic acid,
c) optionally increasing the solids content of the aqueous solution resulting from step b) up to at least 75% by weight of the total weight thereof,
d) carrying out a heat treatment on the aqueous solution resulting from step b) or optionally from step c), at a temperature of between 130° C. and 300° C. under a negative pressure of between 50 and 500 mbar.

The first step of the method according to the invention consists in providing an aqueous solution of carbohydrates, of which 40% to 95% of the dry weight thereof consists of maltose.

Preferably, the other carbohydrates are saccharide compounds of glucose. These carbohydrates may thus be provided in the form of one or more glucose syrups.

According to one quite particularly preferred variant of the invention, said aqueous solution resulting from step a) also contains glucose.

In this step, the maltose and the other carbohydrates may be supplied in the form of dry products (powders) or alternatively in liquid form. When dry products are used, it is appropriate to add water to them so as to produce the aqueous solution which is the subject of step a). The liquid form is referred to as "syrup" and consists of an aqueous solution of at least one carbohydrate. A preferred variant of the invention consists in mixing a syrup containing at least one carbohydrate and at least one carbohydrate in the form of dry product. According to this variant, mixing is facilitated if the temperature is brought to at least 50° C. and at most 90° C.

The aqueous solution resulting from step a) has a solids content of at least 50%, preferably of at least 70%, very preferably of at least 80% by weight of the total weight thereof, and in any case of at most 95% by weight of the total weight thereof.

A particularly preferred syrup of at least one carbohydrate is one in which the distribution of the degrees of polymerization ($D_P$) is as follows:
from 1% to 5% compounds having a degree of polymerization of 1
from 40% to 75% compounds having a degree of polymerization of 2
from 10% to 25% compounds having a degree of polymerization of 3
from 5% to 10% compounds having a degree of polymerization between 4 and 8 inclusive
from 1% to 15% compounds having a degree of polymerization between 9 and 20 inclusive
from 1% to 15% compounds having a degree of polymerization of strictly greater than 20 each of these % being expressed as % of the total weight of the carbohydrates contained in said syrup, and the sum of these % being equal to 100%.

Among the most preferred syrups, mention may be made of the syrup sold by the applicant company under the name Glucose Syrup 5774, the distribution of the degrees of polymerization of which corresponds to the ranges listed above.

Another particularly preferred syrup of at least one carbohydrate is one in which the distribution of the degrees of polymerization ($D_P$) is as follows:
from 8% to 30% compounds having a degree of polymerization of 1
from 40% to 75% compounds having a degree of polymerization of 2
from 7% to 17% compounds having a degree of polymerization of 3
from 3% to 10% compounds having a degree of polymerization between 4 and 8 inclusive
from 0.1% to 5% compounds having a degree of polymerization between 9 and 20 inclusive
from 0.1% to 5% compounds having a degree of polymerization of strictly greater than 20 each of these % being expressed as % of the total weight of the carbohydrates contained in said syrup, and the sum of these % being equal to 100%.

This other syrup may especially be obtained by mixing the glucose syrup 5774 with dextrose in powder form.

The second step of the method according to the invention consists in placing the aqueous carbohydrate solution described above in contact with at least one polyol and at least one inorganic or organic acid. Mixing is facilitated if the temperature of the medium is brought to at least 50° C. and at most 90° C.

The polyol used in the method in accordance with the invention may especially be selected, without however this selection being exhaustive, from glycerol, erythritol, xylitol, arabitol, ribitol, sorbitol, dulcitol, mannitol, maltitol, isomaltitol, lactitol and mixtures thereof, more preferably from sorbitol, mannitol and maltitol, the most preferred polyol being maltitol. The polyol represents 5% to 30%, preferably 5% to 25%, very preferably 5% to 10% by weight of the sum of the dry weights of carbohydrates, of said polyol and of the acid.

The polyol is introduced in the form of an aqueous solution, with a solids content of between 20% and 90%, preferably between 25% and 85%, and very preferably between 30% and 80% by weight of the total weight thereof. Alternatively, the polyol may initially be present in anhydrous form, and in this case it may be dissolved directly by introduction into the syrup containing at least one carbohydrate, or it may be placed in aqueous solution beforehand by being dissolved in water.

The method in accordance with the present invention also employs an inorganic or organic acid, preferably organic, as catalyst for the polymerization reaction. This organic acid may be selected, non-exhaustively, from citric, sulfuric, fumaric, succinic, gluconic and hydrochloric acid and mixtures of these acids, citric acid being the most preferred.

In any case, the acid selected should not be too volatile, and should not be incompatible with, or pose potential risks to, future use in the fields of human food and animal feed.

The amount of acid employed here is between 0.5% and 2%, preferably between 0.5% and 1.5%, and is very preferably approximately 1% by weight of said acid relative to the dry weight of carbohydrates, of the polyol and of said acid. In any case, those skilled in the art will know to adapt the amount of acid employed, especially taking into consideration questions of subsequent neutralization linked to the use of any excess of said acid. The acid in question can be used in the form of an aqueous solution, with a solids content of between 20% and 90%, preferably between 25% and 85%, and very preferably between 30% and 80% by weight of the total weight thereof. Alternatively, said acid may initially be present in anhydrous form, and in this case it may be dissolved directly by introduction into the carbohydrate syrup, or it may be placed in aqueous solution beforehand by being dissolved in water.

Preferably, those skilled in the art employing the method according to the present invention will seek to obtain a solids content for the reaction medium including the mixture of carbohydrates, the polyol and the acid of between 20% and 98%, preferably between 25% and 95%, and very preferably between 30% and 95% by weight of the total weight thereof. Those skilled in the art will know to adapt this solids content, especially as a function of the richness desired for the reaction medium but also, inter alia, taking account of the vicosity of the medium (with regard to any problems of pumpability and/or transfer of the resulting medium). They will also know to adapt it with a view to limiting, or even avoiding if they so wish, the optional step c) consisting in increasing the solids content of the aqueous solution containing the carbohydrates, the polyol and the acid up to at least 75% by dry weight.

The third step of the method according to the invention is optional since it consists, where appropriate, in increasing the solids content of the aqueous solution resulting from step b) up to at least 75% by weight of the total weight thereof. This is carried out in the form of a heat treatment, especially at a temperature of between 60° C. and 150° C., preferably between 80° C. and 120° C. Preferably, a negative pressure of between 50 mbar and 500 mbar, preferably between 100 mbar and 400 mbar, will be applied. The duration of this step is between 4 and 20 hours. Those skilled in the art will know to adapt the parameters of time, temperature and pressure, especially as a function of the initial solids content thereof and of the solids content which they desire to finally obtain. For those skilled in the art, the term "apply a negative pressure" means that the pressure indicated is less than 1 bar absolute pressure, unlike the term "apply a pressure" which means that the pressure is greater than atmospheric pressure. In other words, when a negative pressure of between X mbar and Y mbar is applied, this means that the absolute pressure is between X mbar and Y mbar.

The fourth step of the method according to the invention consists in carrying out a heat treatment on the aqueous solution resulting from step b) or optionally from step c), at a temperature of between 130° C. and 300° C. under a negative pressure of between 50 and 500 mbar. The polymerization reaction occurs under these conditions.

This step is carried out in a polymerization reactor fitted with heating devices and which makes it possible to work at reduced pressure. Such a reactor may especially consist of a curing oven or a vacuum furnace. Alternatively, the operation of adjusting the solids content and of polymerization is carried out in the same reactor, which advantageously has the abovementioned means and devices.

The polymerization reaction is carried out at a temperature of between 130° C. and 300° C., preferably between 150° C. and 200° C. The water generated by the reaction is avacuated continuously by evaporation. This operation is carried out under reduced pressure, especially at a negative pressure of between 50 mbar and 500 mbar. In parallel, said reaction is carried out for a time of between 5 minutes and 4 hours, preferably between 5 minutes and 2 hours.

The reaction temperature and time are interdependent variables. It is advisable to ensure that the temperature is not raised too high, so as to avoid any pyrolysis and/or heat degradation phenomena of the products (since such a degradation may adversely affect the sensory properties of the final food product manufactured). Nonetheless, the reaction time decreases as much as the temperature increases, with a view to complete polymerization. From this point of view, the products according to the present invention may just as well be manufactured at a temperature of the order of 250° C. and with a residence time of 10 minutes, as at a temperature of approximately 180° C. and a residence time of approximately 90 minutes. Using the method of the invention, those skilled in the art may vary the α-1,4-bond content of the total number of 1,4-glycosidic bonds in the following way; the further the reaction progresses, the more this content decreases.

A second subject of the present invention consists of maltooligosaccharides able to be obtained according to the method defined above.

According to a first embodiment, these maltooligosaccharides have a content of α-1,4-bonds of between 70% and 80% of the total number of 1,4-glycosidic bonds. According to a second embodiment, these maltooligosaccharides have a content of α-1,4-bonds of between 65% and 83% of the total number of 1,4-glycosidic bonds and/or a ratio of the total number of 1,4-glycosidic bonds to the total number of 1,6-glycosidic bonds of greater than 1 and/or a content of α-1,6-bonds of between 35% and 58% of the total number of 1,6-glycosidic bonds.

Another subject of the present invention consists of maltooligosaccharides having, according to a first embodiment, a content of α-1,4-bonds of between 70% and 80% of the total number of 1,4-glycosidic bonds. According to a second embodiment, these maltooligosaccharides have a content of α-1,4-bonds of between 65% and 83% of the total number of 1,4-glycosidic bonds and/or a ratio of the total number of 1,4-glycosidic bonds to the total number of 1,6-glycosidic bonds of greater than 1 and/or a content of α-1,6-bonds of between 35% and 58% of the total number of 1,6-glycosidic bonds.

These maltooligosaccharides which are subjects of the present invention may also be characterized in that they have a content of α-1,6-bonds of between 35% and 58% of the total number of 1,6-glycosidic bonds, advantageously between 38% and 52% of the total number of 1,6-glycosidic bonds, preferably between 40% and 50% of the total number of 1,6-glycosidic bonds.

These maltooligosaccharides may also be characterized in that they have a fiber content of between 50% and 70%.

These maltooligosaccharides are also characterized in that they have an amount of glucose released or accessible after enzymatic digestion of between 1% and 12%, more preferably of between 3% and 9%.

According to this second embodiment, the maltooligosaccharides may have a content of α-1,4-bonds of between 65% and 80% of the total number of 1,4-glycosidic bonds, especially of between 65% and 70% of the total number of 1,4-glycosidic bonds.

The maltooligosaccharides of the first embodiment may, like that of the second embodiment, a ratio of the total number of 1,4-glycosidic bonds to the total number of 1,6-glycosidic bonds of greater than 1. Preferably, the maltooligosaccharides of the invention have a ratio of the total number of 1,4-bonds to the total number of 1,6-bonds ranging from 1.03 to 2.50 and for example from 1.05 to 2.

A final subject of the present invention relates to the use of the maltooligosaccharides according to the invention, or able to be obtained according to the method defined above, in human food and animal feed.

Non-limitingly, the maltooligosaccharides according to the invention, or able to be obtained according to the method defined above, may be incorporated into compositions or products intended for ingestion and for oral administration, such as various foodstuffs, for instance confectionery, pastries, ice creams, chewing pastes, chewing gums, drinks, jellies, soups, milk-based preparations, yoghurts, cakes, prepared animal fodder, dietary supplements, pharmaceutical, veterinary, dietary or hygiene products, such as, for example, elixirs, cough syrups, lozenges or tablets, pastilles, oral hygiene solutions, toothpastes and tooth gels.

Maltooligosaccharides of the second embodiment and variants of these maltooligosaccharides:

Embodiment A

Maltooligosaccharides having a content of α-1,4-bonds of between 65% and 83% of the total number of 1,4-glycosidic bonds, a ratio of the total number of 1,4-glycosidic bonds to the total number of 1,6-glycosidic bonds of greater than 1 and a content of α-1,6-bonds of between 35% and 58% of the total number of 1,6-glycosidic bonds.

Embodiment B

Maltooligosaccharides according to embodiment A, also having a ratio of the total number of 1,4-glycosidic bonds to the total number of 1,6-glycosidic bonds ranging from 1.03 to 2.50, for example from 1.05 to 2.

Embodiment C

Maltooligosaccharides according to embodiment A or B, also having a content of α-1,6-bonds of between 38% and 52% of the total number of 1,6-glycosidic bonds, preferably between 40% and 50% of the total number of 1,6-glycosidic bonds.

Embodiment D

Maltooligosaccharides according to one of embodiments A to C, also having a content of α-1,4-bonds of between 65% and 80% of the total number of 1,4-glycosidic bonds.

Embodiment E

Maltooligosaccharides having a content of α-1,4-bonds of between 65% and 80% of the total number of 1,4-glycosidic bonds and a ratio of the total number of 1,4-glycosidic bonds to the total number of 1,6-glycosidic bonds of greater than 1.

Embodiment F

Maltooligosaccharides according to embodiment E, also having a content of α-1,6-bonds of between 35% and 58% of the total number of 1,6-glycosidic bonds, advantageously between 38% and 52% of the total number of 1,6-glycosidic bonds, preferably between 40% and 50% of the total number of 1,6-glycosidic bonds.

Embodiment G

Maltooligosaccharides according to one of embodiments E and F, also having a ratio of the total number of 1,4-glycosidic bonds to the total number of 1,6-glycosidic bonds ranging from 1.03 to 2.50, for example from 1.05 to 2.

Embodiment H

Maltooligosaccharides having a content of α-1,4-bonds of between 65% and 83% of the total number of 1,4-glycosidic bonds and a content of α-1,6-bonds of between 35% and 52% of the total number of 1,6-glycosidic bonds.

Embodiment I

Maltooligosaccharides according to embodiment H, also having a ratio of the total number of 1,4-glycosidic bonds to the total number of 1,6-glycosidic bonds of greater than 1, advantageously ranging from 1.03 to 2.50, for example from 1.05 to 2.

Embodiment J

Maltooligosaccharides according to embodiment H or I, also having a content of α-1,6-bonds of between 38% and 52% of the total number of 1,6-glycosidic bonds, preferably between 40% and 50% of the total number of 1,6-glycosidic bonds.

Embodiment K

Maltooligosaccharides according to one of embodiments H to J, also having a content of α-1,4-bonds of between 65% and 80% of the total number of 1,4-glycosidic bonds.

Embodiment L

Maltooligosaccharides according to one of embodiments A to K, also having a fiber content of between 50% and 70%.

Embodiment M

Maltooligosaccharides according to one of embodiments A to L, also having a content of α-1,4-bonds of between 65% and 70% of the total number of 1,4-glycosidic bonds.

Embodiment N

Maltooligosaccharides according to one of embodiments A to M, also having an amount of glucose released or accessible after enzymatic digestion of between 1% and 12%, more preferably of between 3% and 9%.

The examples which follow make it possible to better understand the present invention, without however limiting the scope thereof.

Examples

Experimental Methods

Throughout the present application, the contents of glycosidic bonds are determined by NMR, and by the Hakomori method.

NMR makes it possible to access the proportions of α-1,4- and α-1,6-bonds on the one hand, and the other glycosidic bonds on the other.

The Hakomori method makes it possible to access the contents of total 1,4-, 1,6-, 1,2- and 1,3-glycosidic bonds.

Regarding NMR, an Avance III Fourier transform spectrometer (Bruker Spectrospin) operating at 400 MHz and 60° C. and using 5 mm NMR tubes is used. More generally speaking, it is possible to use any other Fourier transform spectrometer, as long as said spectrometer is fitted with all the accessories enabling the production and utlization of a proton spectrum, and also with an accessory which makes it possible to work at temperatures greater than room temperature. Deuterated water, or $D_2O$ (min. 99%), from Euriso Top (CEA Group, Gif-sur-Yvette, France), and sodium salt of 3-trimethylsilyl-1-propanesulfonic acid or TSPSA (Aldrich, ref. 178837) are used.

The procedure for the experiments is as follows:
Introduce 10 mg of sample and 0.75 ml of $D_2O$ into an NMR tube.
Seal the tube, mix, then place in a water bath.
After dissolution, remove the tube from the water bath and let it cool to room temperature.
Add 50 μl of a 10 mg/g solution of TSPSA in $D_2O$.
Adjust the spinner on the tube and place everything in the magnet.
Carry out acquisition, without solvent suppression, with a relaxation time of at least 10 s and without rotation, following suitable instrument settings (field, lock phase and shims). Use a spectral window of between at least −0.1 ppm and 9 ppm, referring to the signal for the methyls of the TSPSA calibrated to 0 ppm.

Use is made of the spectrum after Fourier transformation, phase correction and subtraction of the base line in manual mode (without exponential multiplication; LB=GB=0). Use is made of the results in the following manner:
Integrating the signals; reference may especially be made to figure 1/2 for the limits of integration.
Standardizing the signal S5 to 600, this signal corresponding to the non-exchangeable protons of an anhydroglucose unit ($H_2$, $H_3$, $H_4$, $H_5$ and $2H_6$); the rest of the signal corresponding to all the $H_1$ protons (reducing end groups and bonds).
Taking the values of S1 ($H_1$ α (1,4)), S2 ($H_1$ reducing α) and S3 ($H_1$ α (1,6)).
Determining the S4 β-reducers by performing the operation S2×0.6/0.4.
Calculating S6 by performing the operation S6=100−(S1+S2+S3+S4).
Determining the proportions of α-(1,4)-, α-(1,6)- and other bonds by calculating the sum of the 3 respective surface areas (S1, S3 and S6) and by standardizing them to 100 to express them in % (i.e. % i=Si×100/(S1+S3+S6)).

TABLE 1

| Integrated surface area | Limits of integration (in ppm) | | Types of bonds |
|---|---|---|---|
| S1 | 5.45 | 5.26 | $H_1$ α-(1,4) |
| S2 | 5.26 | 5.19 | $H_1$ α-reducers |
| S3 | 5.04 | 4.88 | $H_1$ α-(1,6) |
| S5 | 4.32 | 3.10 | Other protons ($H_2$, $H_3$, $H_4$, etc.) i.e. 6 protons |

The Hakomori method is that described in the 1964 publication J. Biol. Chem., 55, 205.

Throughout the present application, the amount of glucose released or accessible after enzymatic digestion is determined according to the following method:
Weigh out 0.3 g dry weight of product to be tested.
Add 75 ml of 0.1 mol/l Na maleate buffer, pH 7.00 (Fluka, reference 63180).
Stir until the product dissolves.
Place the flasks in a water bath for 15 minutes, so that the temperature of the solution is 37° C.
Take a sample of 0.75 ml of the initial solution and add 0.075 g of porcine pancreatin (Sigma, reference P7545) following the sampling of the initial solution; this operation corresponds to the start of timing.
Incubate at 37° C. in a thermostated bath with stirring for 30 minutes.
Take a sample of 0.75 ml.
Add 0.40 g of rat intestinal mucosa (Sigma, reference 11630).
Incubate for 3 h 30 at 37° C. in a thermostated bath with stirring.
Over the course of these 3 h 30, take samples of 0.75 ml at 60, 120, 180 and 240 minutes.
Stop the enzymatic reaction by placing the samples taken in a dry bath at 100° C. for 10 minutes.
Carry out a glucose assay on the samples taken (GOD standard enzymatic method).
Calculate the amount of glucose released during digestion of the product after the 3 h 30 (expressed in %): glucose concentration in g/l of the sample taken×(100/product solids)×volume of digest in ml/1000)×(100/weight of wet product in g).

Throughout the present application, the fiber content is measured according to AOAC method 2001-03.

Products According to the Invention

In tests nos. 1 to 5, 5 products were produced according to the method in accordance with the present invention.

A glucose syrup 5774 (Flolys D57), sold by Roquette, with 85% solids content, is used.

This syrup is diluted to 50° Bx.

1 kilo of material is prepared with the weight % mentioned in the table below, in a glass beaker. Said beaker is placed on a hotplate with stirring using a magnetic stirrer bar set to 500 rpm, the temperature being set to 60° C.

Once this temperature has been reached, the glucose sold under the name Dextrose Anhyde C [Anhydrous Dextrose C] by Roquette is added in powder form to the beaker.

The following products are then added in powder form to this aqueous solution:
the maltitol sold under the name SweetPearl P200 by Roquette
the citric acid sold by Sigma, with a purity of greater than or equal to 99.5%.

The weight % of the constituents are given in table 2 for tests nos. 1, 2, 3, 4 and 5 which represent the invention.

TABLE 2

| Test No. | 1 | 2 | 3 | 4 | 5 |
|---|---|---|---|---|---|
| Flolys D57 (85% solids) | 81 | 68 | 68 | 72 | 71 |
| Glucose | 9 | 22.2 | 22.2 | 18 | 18 |
| Maltitol | 9 | 8.9 | 8.9 | 9 | 9 |
| Citric acid | 1 | 0.9 | 0.9 | 1 | 2 |

After complete dissolution of the powders, i.e. after a few minutes, the mixture is clear.

A sample of 120 grams of the mixture is then taken and transferred to an aluminum tray sold by Pro-Jet under reference KPL1001.

The trays are placed in a vacuum furnace for 20 hours at 80° C. then 6 hours at 120° C. A negative pressure of 125 mbar is applied in the furnace. 95.0% solids is then obtained.

The trays with the dry product are then placed in a second furnace heated beforehand to 200° C., everything being placed under a negative pressure of 125 mbar. The trays are removed 90 minutes later. The product is then diluted with water to 30% solids.

For each of the 5 tests above, the applicant determined:
the % of α-1,4-glycosidic bonds of the total number of 1,4-glycosidic bonds
the % of α-1,6-glycosidic bonds of the total number of 1,6-glycosidic bonds
the ratio of the total number of 1,4-glycosidic bonds to the total number of 1,6-glycosidic bonds
the fiber content in %
the amount of glucose released in %.

Products not According to the Invention

The applicant also determined these same parameters for the following products:
NUTRIOSE FB06 sold by the applicant company (test no. 4)
NUTRIOSE FB10 sold by the applicant company (test no. 5)
LITESSE ULTRA sold by Dupont Danisco (test no. 6)
PROMITOR 70 sold by Tate & Lyle (test no. 7)
PROMITOR 85 sold by Tate & Lyle (test no. 8)
FIBERSOL-2 sold by Matsutani (test no. 9)
IMO 500 sold by (test no. 10)

Figure 2:
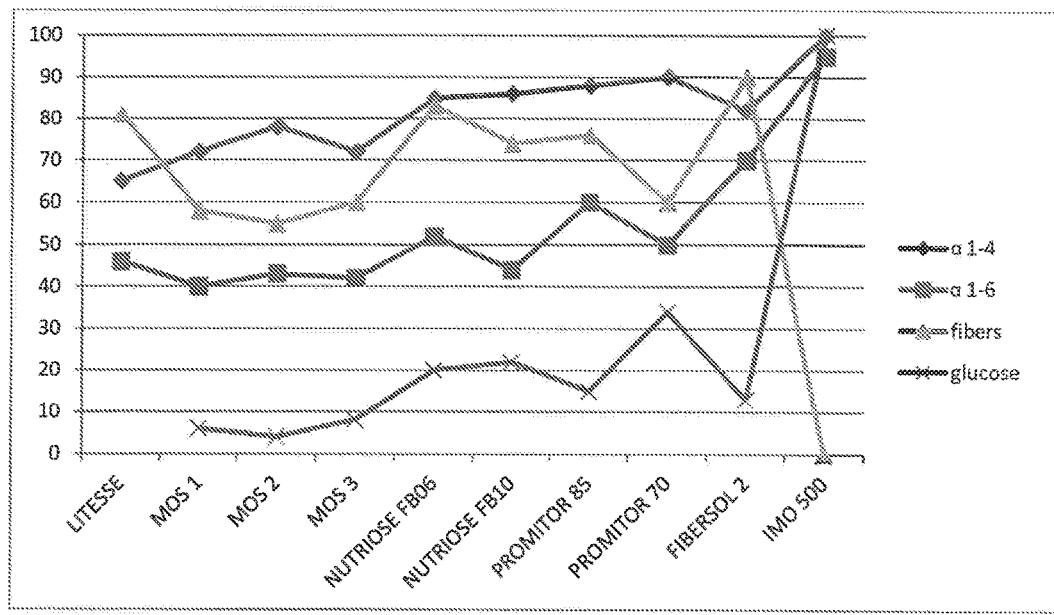
FIG. 2 shows results of products not according to the invention.

All the results have been given in table 3 and on figure 2/2, except for MOS 4 and MOS 5.

TABLE 3

| Product | α-1,4 (%) | α-1,6 (%) | 1,4-/1,6- ratio | Fibers (%) | Glucose (%) |
|---|---|---|---|---|---|
| LITESSE | 67 | 53 | 0.61 | 81 | — |
| MALTOOLIGOSACCHARIDE 1 (MOS 1) | 72 | 40 | 2.11 | 58 | 6 |
| MALTOOLIGOSACCHARIDE 2 (MOS 2) | 78 | 43 | 1.37 | 55 | 4 |
| MALTOOLIGOSACCHARIDE 3 (MOS 3) | 72 | 42 | 1.10 | 60 | 8 |
| MALTOOLIGOSACCHARIDE 4 (MOS 4) | 66 | 42 | 1.45 | 65 | — |
| MALTOOLIGOSACCHARIDE 5 (MOS 5) | 81 | 56 | 1.40 | 62 | — |
| NUTRIOSE FB06 | 85 | 52 | 2.06 | 83 | 20 |
| NUTRIOSE FB10 | 86 | 44 | 1.75 | 74 | 22 |
| PROMITOR 85 | 88 | 60 | 1.15 | 76 | 15 |
| PROMITOR 70 | 90 | 50 | 1.73 | 60 | 34 |
| FIBERSOL-2 | 82 | 70 | 2.11 | 90 | 13 |
| IMO 500 | 100 | 95 | 1.34 | 0 | 100 |

It is possible to observe, remarkably, that all the fiber-rich commercial products belonging to the prior art have a content of α-1,4-glycosidic bonds of greater than 80%, with this content being within a very restricted range of between 80% and 90%.

Moreover, all these products have a fiber content of at least 60%, in most cases at least 75%, and an amount of available glucose which is systematically greater than 10%, in most cases greater than 15% and even sometimes greater than 20%.

Conversely, the 5 products according to the invention have a content of α-1,4-glycosidic bonds of between 66% and 81%. It is observed that, particularly advantageously, these products have high fiber-richness, since said richness is at around 60%. Finally, 3 products according to the invention have a very low content of available glucose, at levels never before achieved. This is particularly surprising due to the fact that although these novel products are fiber-rich, they have a lower content of these fibers than the other products tested. Thus, only these products have the ideal compromise between a product that is relatively fiber-rich and therefore perfectly suited to healthy balanced diets, and a product with a very low glucose bioavailibility with regard to the organism and therefore perfectly suited to diabetic patients or those following diets aiming to reduce sensitivity to this pathological condition.

The invention claimed is:

1. A method for manufacturing maltooligosaccharides having a content of α-1,4-bonds of between 65% and 83% of the total number of 1,4-glycosidic bonds a ratio of the total number of 1,4-glycosidic bonds to the total number of 1,6-glycosidic bonds of greater than 1 and lower to 2.50 and a content of α-1,6-bonds of between 35% and 58% of the total number of 1,6-glycosidic bonds, comprising the steps consisting of:
   a) providing an aqueous solution of at least two carbohydrates, characterized in that 40% to 95% of the dry weight of said solution consists of maltose,
   b) placing the aqueous solution resulting from step a) in contact with at least one polyol and at least one inorganic or organic acid,
   c) optionally increasing the solids content of the aqueous solution resulting from step b) up to at least 75% by weight of the total weight thereof, and
   d) carrying out a heat treatment on the aqueous solution resulting from step b) or optionally from step c), at a temperature of between 140° C. and 300° C. under a negative pressure of between 50 and 500 mbar.

2. The method as claimed in claim 1, characterized in that the aqueous solution resulting from step a) contains glucose.

3. The method as claimed in claim 1, characterized in that the aqueous solution resulting from step a) has a solids content of at least 50% by weight of the total weight thereof.

4. The method as claimed in claim 1, characterized in that the polyol is selected from glycerol, erythritol, xylitol, arabitol, ribitol, sorbitol, dulcitol, mannitol, maltitol, isomaltitol, lactitol and mixtures thereof.

5. The method as claimed in claim 1, characterized in that, when the acid is organic, it is selected from citric, sulfuric, fumaric, succinic, gluconic and hydrochloric acid and mixtures of these acids.

6. The method as claimed in claim 1, characterized in that step c) is carried out in the form of a heat treatment at a temperature of between 60° C. and 150° C.

7. The method as claimed in claim 6, characterized in that step c) is carried out under a negative pressure of between 50 mbar and 500 mbar.

8. The method as claimed in claim 1, characterized in that step d) is carried out at between 150° C. and 200° C.

9. The method as claimed in claim 8, characterized in that step d) is carried out at a pressure of between 50 mbar and 500 mbar.

10. Maltooligosaccharides obtained according to the method of claim 1.

11. The maltooligosaccharides as claimed in claim 10, characterized in that they have a fiber content of between 50% and 70%.

12. The maltooligosaccharides as claimed in claim 10, characterized in that they have an amount of glucose released or accessible after enzymatic digestion of between 1% and 12%.

13. Maltooligosaccharides having a content of α-1,4-bonds of between 65% and 83% of the total number of 1,4-glycosidic bonds, a ratio of the total number of 1,4-glycosidic bonds to the total number of 1,6-glycosidic bonds of greater than 1 and lower than 2.50 and a content of α-1,6-bonds of between 35% and 58% of the total number of 1,6-glycosidic bonds.

14. The maltooligosaccharides as claimed in claim 13, characterized in that they have a content of α-1,6-bonds of between 38% and 52% of the total number of 1,6-glycosidic bonds.

15. The maltooligosaccharides as claimed in claim 13, characterized in that they have a fiber content of between 50% and 70%.

16. The maltooligosaccharides as claimed in claim 13, characterized in that they have an amount of glucose released or accessible after enzymatic digestion of between 1% and 12%.

17. A food composition comprising the maltooligosaccharides of claim 10.

18. The food composition of claim 17, wherein the food composition is a human food.

19. The food composition of claim 17, wherein the food composition is an animal feed.

20. The maltooligosaccharides as claimed in claim 10, characterized in that they have a content of α-1,4-bonds of between 70% and 80% of the total number of 1,4-glycosidic bonds.

21. The maltooligosaccharides as claimed in claim 13, characterized in that they have a content of α-1,4-bonds of between 70% and 80% of the total number of 1,4-glycosidic bonds.

\* \* \* \* \*